United States Patent [19]

Rodewald

[11] 4,402,867

[45] Sep. 6, 1983

[54] SILICA-MODIFIED ZEOLITE CATALYSTS

[75] Inventor: Paul G. Rodewald, Rocky Hill, N.J.

[73] Assignee: Mobil Oil Corporation, New York, N.Y.

[21] Appl. No.: 333,365

[22] Filed: Dec. 22, 1981

[51] Int. Cl.³ ............................................. B01J 29/28
[52] U.S. Cl. ................................................ 252/455 Z
[58] Field of Search ........................... 252/455 Z, 428

[56] References Cited

U.S. PATENT DOCUMENTS

| | | | |
|---|---|---|---|
| 3,725,302 | 4/1973 | Shimely et al. | 252/455 Z |
| 4,100,219 | 7/1978 | Rodewald | 252/455 Z |
| 4,138,363 | 2/1979 | Hertzenberg et al. | 252/455 Z |

Primary Examiner—Carl F. Dees
Attorney, Agent, or Firm—Alexander J. McKillop; Michael G. Gilman; Dennis P. Santini

[57] ABSTRACT

An improved method is provided for the production of silica-modified zeolite catalysts. Such catalysts are especially useful in a wide variety of processes including the conversion of methanol to gasoline, methanol to olefins, selective toluene disproportionation, toluene alkylation with methanol, the synthesis of p-ethyl toluene, lubricant hydro-dewaxing and the like. The catalysts formed in accordance with the present invention comprise crystalline aluminosilicate zeolites having a silica to alumina ratio of at least about 12, a constraint index, as hereinafter defined, within an approximate range of 1–12 and having contained within the interior crystalline structure thereof added amorphous silica in an amount of at least about 0.3% and preferably between about 0.5% and about 30 weight percent. The resultant catalyst is characterized by an n-hexane sorption capacity at a temperature of 90° C. and an n-hexane partial pressure of 83 mm. of mercury which is at least 1 percent less than corresponding sorption capacity under identical conditions for the unmodified zeolite. Generally, the n-hexane sorption capacity for the described silica-modified zeolite, at the above specified conditions, is 5 to 60 percent less than that for the zeolite which has not undergone treatment to incorporate amorphous silica therein. The invention described herein also encompasses synthesis of the specified catalyst and use of the same in, for example, selectively converting lower monohydric alcohols and their ethers, especially methanol and dimethyl ether, to a hydrocarbon mixture rich in ethylene and propylene.

17 Claims, No Drawings

SILICA-MODIFIED ZEOLITE CATALYSTS

BACKGROUND OF THE INVENTION

1. Field of the Invention

The present invention relates to a crystalline aluminosilicate catalyst having added silica contained within its interior structure, the manufacture of such catalyst and the use thereof.

2. Description of the Prior Art

U.S. Pat. No. 2,722,504 describes a catalyst of an activated oxide such as silica gel having a thin layer of an organosilicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. No. 3,682,996 to Kerr and in U.S. Pat. No. 3,698,157 to Allen et al. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites, modified by treatment with an organic-radical substituted silane are described, together with the use of such modified zeolites in chromotographic separation of the compounds contained in a C aromatic feed stock.

U.S. Pat. No. 4,145,315 discloses a method for the production of silica modified zeolite catalysts which are prepared by contacting the specific zeolite with an organic solvent solution such as hexane, of a silicone fluid, distillation of the hexane, and air calcination of the zeolite residue.

SUMMARY OF THE INVENTION

In accordance with the present invention, there has been discovered an improved method for the production of a silica-modified zeolite catalyst which is particularly applicable for selectively producing low molecular weight olefins from low molecular weight alcohols and/or ethers, the conversion of methanol to gasoline, as well as a wide variety of other conversions including selective toluene disproportionation, toluene alkylation with methanol, p-ethyl toluene synthesis and lubricant hydro-dewaxing and the like.

The catalyst produced in accordance with the method of the present invention comprises a crystalline aluminosilicate zeolite having a silica to alumina ratio of at least about 12, a constraint index within the approximate range of 1 to 12 and containing within the interior crystalline structure of said zeolite, amorphous silica added to the crystalline zeolite subsequent to the latter's formation in an amount of at least about 0.3 weight percent and generally in the approximate range of 0.5 to 30 weight percent. The resulting catalyst has a sorption capacity, as determined by n-hexane sorption at 90° C. and a partial pressure of 83 mm of mercury, which is at least 1 percent and generally 5 to 60 percent less than that of the unmodified zeolite.

It has been found that such catalyst is suitably prepared by sorption of an aqueous dispersion of a silicon-containing compound into the porese of a crystalline aluminosilicate zeolite having the above-specified silica/alumina ratio and constraint index characteristics. The molecular dimensions of the silicon compound employed are such that it is readily sorbed into the pores of the crystalline aluminosilicate zeolite having the above-specified silica/alumina ratio and constraint index characteristics. The sorbed silicon compound contained in the pores of the crystalline aluminosilicate is subjected to calcination in an oxygen-containing atmosphere, such as air at a temperature in excess of about 300° C. but below a temperature at which crystallinity of the zeolite is adversely affected, generally between about 300° C. and about 700° C. to yield amorphous silica within the pores of the crystalline aluminosilicate zeolite.

The catalyst, so produced, is highly effective in converting low molecular weight alcohols or ethers derived therefrom, to an olefin rich hydrocarbon product. Thus, utilizing methanol as the feed, a representative hydrocarbon product composition is 50–75 percent olefins, 15–30 percent aromatics and remainder paraffins. Ethylene and propylene constitute approximately 75 percent of the olefin product with an ethylene/propylene ratio of greater than one. The xylene fraction of the aromatics produced is enriched in para-xylene very substantially over the normal equilibrium concentration of 24 weight percent.

Reaction conditions for carrying out the above specified selective conversions include a temperature between about 250° C. and about 600° C., a pressure between about 0.2 and about 30 atmospheres utilizing a feed liquid hourly space velocity (LHSV) between about 0.1 and about 50. The latter LHSV is based upon the volume of catalyst composition, i.e., total volume of active catalyst and binder therefor. The effluent is separated to remove the desired products, e.g., ethylene, propylene butene and paraxylene and unreacted material may be recycled for further reaction.

DESCRIPTION OF SPECIFIC EMBODIMENTS

The catalytic composition produced by the method of this invention comprises a crystalline aluminosilicate zeolite characterized by a silica to alumina ratio of at least about 12, preferably in excess of 30, and a constraint index within the approximate range of 1 to 12. This zeolite has contained within the interior crystalline structure thereof added amorphous silica in an amount of at least 0.3 weight percent as a result of sorbing a silicon-containing compound into the pores of the zeolite and calcining.

The crystalline zeolites produced herein are members of a class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also inclusded within this definition are substantially pure silica species of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-B 12, ZSM-23, ZSM-35, ZSM-38, ZSM-48, and other similar materials.

ZSM-5 is described in greater detail in U.S. Pat. No. 3,702,886 and Re 29,948. The entire description contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)$M_{2/n}$O:(0.2)$Al_2O_3$:(100)$SiO_2$ wherein:
M is at least one cation having a valence n; and
RN is a $C_1$–$C_{20}$ organic compound having at least one amine functional group of $pK_a \geq 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiometry to $2 RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+$(added) $SiO_2$ | = | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pk_a \geq 7$, as defined above, and includes such compounds as $C_3$–$C_{18}$ primary, secondary, and tertiary amines, cyclic amine (such as piperdine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identifiction of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeters. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include boty synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The crystals of zeolite in a form substantially free of alkali metal, i.e., containing less than about 1.5 weight percent alkali metal and preferably having at least a portion of the original cations associated therewith replaced by ammonium and/or hydrogen, are then contacted with a silicon-containing compound of molecular dimensions such that it is readily sorbed into the pores of the zeolite. Representative and preferred silicon-containing compounds include silicones of a molecular size capable of entering the pores of the zeolite. The silicone compound utilized is characterized by the general formula:

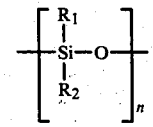

where $R_1$ and $R_2$ are individually selected from the group consisting of hydrogen, methyl, fluorine, chlorine and hydroxy and n is an integer of at least 3 and generally in the range of 4 to 1000. The molecular weight of the silicone compound employed is generally between about 250 and about 60,000 and preferably within the approximate range of 300 to 20,000. Representative silicone compounds include methylhydrogensilicone, dihydrogen silicone, dimethyl silicone, dichlorosilicone, fluorohydrogen silicone and difluorosilicone.

Silicone compounds are preferred as sources of silica in modification of the zeolite catalysts described herein since the zeolites so modified have been found to provide selective conversion of low molecular weight alcohols to light olefins with extremely low production of undesirable $C_{10+}$ hydrocarbons, e.g., durene. Another silicon-containing compound which may be employed is a silane having the following formula:

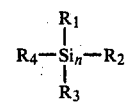

where n is an integer of from 1 to 10; $R_1$ and $R_2$ are hydrogen, fluorine, chlorine, methyl, ethyl, amino, methoxy or ethoxy; $R_3$ is hydrogen, fluorine, chlorine, methyl, amino or methoxy; and $R_4$ is hydrogen or fluorine. Other suitablwe silanes include poly-silanes, such as di-silanes, tri-silanes and higher silanes, up to deca-silanes. It is also contemplated to use derivatives of the aforenoted poly-silanes having methyl, chloro or fluoro substituents.

In accordance with the present invention, the silicone compound employed is in the form of an aqueous emulsion under the conditions of contact with the zeolite. The pores of the latter are preferably, but not necessarily, saturated with the contacting media containing the silica compound when a silicone compound is employed. Contact between the aqueous silicone emulsion and the zeolite is maintained at a temperature between about 10° C. and about 200° C. for a period of time sufficient to sorb the ultimately desired amount of silicone therein. The time of contact will generally be within the range of 0.2 to 5 hours, during which time the mixture is desirably subjected to evporation so that the aqueous silicone emulsion process water may be vented to the atmosphere. The resulting residue is then calcined in an oxygen-containing atmosphere, preferably air, at a rate of 0.2° C. to 5° C. per minute to a temperature greater than 300° C. but below a temperature at which the crystallinity of the zeolite is adversely affected. Generally, such temperature will be below 700° C. Preferably the temperature of calcination is within the approximate range of 350° C. to 550° C. The product is maintained at the calcination temperature usually for 1 to 24 hours to yield a zeolite having a silica contained in the interior porous structure thereof.

The amount of silica incorporated with the zeolite will depend on several factors. One of these is the time that the zeolite and the silicon-containing source are maintained in contact with each other. With greater contact times, all other factors being equal, a greater amount of silica is incorporated with the zeolite. Other factors upon which the amount of silica incorporated with the zeolite is dependent include temperature, concentration of the treating compound in the contacting media, the degree to which the zeolite has been dried prior to contact with the silicon-containing compound, and calcination of the zeolite after contact of the same with the treating compound and the amount and type of binder incorporated with the zeolite. Generally, the amount of silica contained in the interior porous structure of the zeolite will be between about 0.3 and about 40 and preferably between about 0.5 and about 30 weight percent.

The amount of silica incorporated into the zeolite crystal can be assessed from a reduction in the zeolite sorption capacity. The latter is determined from the amount of n-hexane sorbed at a temperature of 90° C. and a n-hexane partial pressure of 83 mm mercury and is determined from the increase in zeolite weight upon sorption. The decrease in sorption capacity of the zeolite under the above conditions attributable to the presence of added amorphous silica is at least 1 percent and generally in the range of 5 to 60 percent. Representative sorption data for a binder-free zeolite and an alumina-zeolite extrudate are shown below:

| Binder-Free ZSM-5 | Mg. n-hexane Sorbed Per Gram of ZSM-5 |
|---|---|
| No added amorphous silica | 105 |
| Intracrystalline amorphous silica (24%) | 55 |
| Extrudate-65% ZSM-5-35% Al$_2$O$_3$ | |
| No added amorphous silica | 80 |
| Intracrystalline amorphous silica (14%) | 61 |

The catalysts which are obtained utilizing the improved method of the present invention are suitable for employment in processes where the conversion is carried out in vapor phase by contact in a reaction zone, such as, for example, a fixed bed of catalyst, under effective conversion conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions.

The conversion process described herein may be carried out as a batch-type, semi-continuous or continuous operation utilizing a fixed or moving bed catalyst zone wherein the charge is passed concurrently or countercurrently through a moving fluidized bed of the catalyst. The fluidized catalyst after use is conducted to a regeneration zone wherein coke is burned from the catalyst in an oxygen-containing atmosphere, e.g., air, at an elevated temperature, after which the regeneration catalyst is recycled to the conversion zone for further contact with the charge.

The following examples will serve to illustrate methods for the preparation of the silica modified zeolite catalyst and conversion processes which such catalysts are particularly suited for.

EXAMPLE I

Preparation Of A Silica-modified Zeolite

Four (4.00) grams of an NH$_4$ZSM-5 extrudate of 1–2 micron crystal size (14/30 mesh) and containing 35 weight percent of alumina and 65 weight percent of the zeolite were added to 1.12 grams of a 40% methylhydrogen silicone aqueous emulsion diluted with 40 cc water. After distillation of the water, the residue was heated for 1 hour at 100° C. and then program air-calcined at 1° C./minute to 538° C., then 7 hours at 538° C. The resultant catalyst contained a nominal 10% silica.

EXAMPLE II

| Conversion of Methanol to Gasoline Over Silica-Modified HZSM-5 (10% SiO$_2$) | | | |
|---|---|---|---|
| Impregnation Mode | Hexane Solution | Aqueous Emulsion | Fresh HZSM-5 |
| Temp., °C. | 397 | 388 | 388 |
| WHSV | 2.0 | 2.0 | 2.0 |
| % of Hydrocarbons | | | |
| C$_5$+ | 62 | 58 | 64 |
| Aromatics | 25 | 22 | 27 |
| Durene | 2.2 | 2.0 | 4 |

EXAMPLE III

| Conversion of Methanol to Ethylene Over Silica-Modified HZSM-5 | | | |
|---|---|---|---|
| Impregnation Mode | Hexane Solution | Aqueous Emulsion | Fresh HZSM-5 |
| Temp., °C. | 340 | 350 | 340 |
| % Silica | 14 | 10 | — |
| Conversion, Wt. % | Ethylene Selectivity, Wt. % | | |
| 28 | 31 | 31 | 27 |
| 47 | 28 | 29 | 24 |
| 57 | 27 | 29 | 23 |

As hereinbefore noted processes which employ the catalysts which are produced in accordance with the improved method of the present invention include the conversion of lower monohydric alcohols having up to four carbon atoms, and their ethers, especially methanol and dimethyl ether, to a hydrocarbon mixture rich in C$_2$–C$_3$ olefins, by contact, under conversion conditions, with the above-described catalyst. It has been found that such catalyst affords a substantially higher selectivity for ethylene production over corresponding use of zeolite which has not undergone modification by silica addition. It has further been found that with the catalysts described herein, only moderate amounts of durene are formed during the desired alcohol and/or ether conversion. As is well known, durene is an undesirable component in gasoline, tending to crystallize in the carburetor of an internal combustion engine causing the latter to stall. High durene make, usually associated with low operating temperatures during conversion of low molecular weight alcohols, has not been observed using the catalysts described herein.

As shown by the data contained in the foregoing examples, for the conversion of methanol to hydrocarbons, the silica-modified catalysts prepared by solvent solutions thereof such as hexane solutions or those silica-modified catalysts prepared in accordance with the method of the present invention, i.e., catalyst preparation utilizing aqueous silicone emulsions, showed similar hydrocarbon products including a 50% reduction in durene. The advantages for catalyst preparation in accordance with the present invention include the fact that an aqueous emulsion of the silicone fluid may be substituted for a organic solution thereof in the preparation of the catalyst with economic advantages that on a commercial scale are quite significant. Additionally, it will be noted that as hereinbefore described the process water used in the silicone emulsion may be vented to the atmosphere whereas organic solvents such as hexane may not and must be condensed to avoid hydrocarbon emissions.

What is claimed is:

1. A method for preparing a composition comprised of a crystalline zeolite having amorphous silica contained within its interior crystalline structure which comprises
    contacting a crystalline zeolite, characterized by a silica to alumina mole ratio of at least about 12, a constraint index within the approximate range of 1 to 12 and, after heating at 540° C. for 1 hour in an inert atmosphere, an intracrystalline sorption capacity for normal hexane which is greater than that for water, with an aqueous emulsion of a silicon-containing compound selected from the group consisting of silanes and silicones, said silicon-containing compound having molecular dimensions such that it enters the pores of said zeolite, at a temperature of from about 10° C. to about 200° C. for a time sufficient to permit sorption into the pores of said zeolite of sufficient aqueous emulsion to provide at least about 0.3 weight percent amorphous silica within its interior crystalline structure upon calcination in an oxygen-containing atmosphere at a temperature of from about 300° C. to about 700° C., and
    calcining the aqueous emulsion contacted crystalline zeolite in an oxygen-containing atmosphere at a temperature of from about 300° C. to about 700° C. to yield said composition.

2. The method of claim 1 wherein said crystalline zeolite has the structure of ZSM-5, ZSM-11, ZSM-12, ZSM-23, ZSM-35, ZSM-38 or ZSM-48.

3. The method of claim 2 wherein said crystalline zeolite has the structure of ZSM-5.

4. The method of claim 1 wherein said silicones are characterized by the general formula:

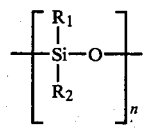

wherein $R_1$ and $R_2$ are individually selected from the group consisting of hydrogen, methyl, fluorine, chlorine and hydroxy and n is an integer of at least 3.

5. The method of claim 1 wherein said silanes are characterized by the general formula:

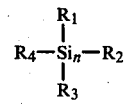

wherein n is an integer of from 1 to 10; $R_1$ and $R_2$ are hydrogen, fluorine, chlorine, methyl, ethyl, amino, methoxy or ethoxy; $R_3$ is hydrogen, fluorine, chlorine, methyl, amino or methoxy; and $R_4$ is hydrogen or fluorine.

6. The method of claim 4 wherein n is an integer of from 4 to 1000.

7. The method of claim 4 wherein said silicones are selected from the group consisting of methylhydrogen silicone, dihydrogen silicone, dimethylsilicone, dichlorosilicone, fluorohydrogen silicone and difluorosilicone.

8. The method of claim 7 wherein said silicone is methylhydrogen silicone.

9. The method of claim 1 wherein said calcining is conducted at a temperature from about 350° C. to about 550° C.

10. A composition prepared by the method comprising
    contacting a crystalline zeolite, characterized by a silica to alumina mole ratio of at least about 12, a constraint index within the approximate range of 1 to 12 and, after heating at 540° C. for 1 hour in an inert atmosphere, an intracrystalline sorption capacity for normal hexane which is greater than that for water, with an aqueous emulsion of a silicon-containing compound selected from the group consisting of silanes and silicones, said silicon-containing compound having molecular dimensions such that it enters the pores of said zeolite, at a temperature of from about 10° C. to about 200° C. for a time sufficient to permit sorption into the pores of said zeolite of sufficient aqueous emulsion to provide at least about 0.3 weight percent amorphous silica within its interior crystalline structure upon calcination in an oxygen-containing atmosphere at a temperature of from about 300° C. to about 700° C.

11. The composition of claim 10 wherein said crystalline zeolite has the structure of ZSM-5, ZSM-11, ZSM-12, ZSM-23, ZSM-35, ZSM-38 or ZSM-48.

12. The composition of claim 11 wherein said crystalline zeolite has the structure of ZSM-5.

13. The composition of claim 10 wherein said silicones are characterized by the general formula:

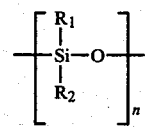

wherein $R_1$ and $R_2$ are individually selected from the group consisting of hydrogen, methyl, fluorine, chlorine and hydroxy and n is an integer of at least 3.

14. The composition of claim 10 wherein said silanes are characterized by the general formula:

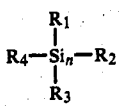

wherein n is an integer of from 1 to 10; $R_1$ and $R_2$ are hydrogen, fluorine, chlorine, methyl, ethyl, amino, methoxy or ethoxy; $R_3$ is hydrogen, fluorine, chlorine, methyl, amino or methoxy; and $R_4$ is hydrogen or fluorine.

15. The composition of claim 13 wherein n is an integer of from 4 to 1000.

16. The composition of claim 13 wherein said silicones are selected from the group consisting of methylhydrogen silicone, dihydrogen silicone, dimethylsilicone, dichlorosilicone, fluorohydrogen silicone nad difluorosilicone.

17. The composition of claim 16 wherein said silicone is methylhydrogen silicone.

* * * * *